United States Patent [19]
Bosetti et al.

[11] Patent Number: 6,034,265
[45] Date of Patent: Mar. 7, 2000

[54] PROCESS FOR THE SYNTHESIS OF AROMATIC URETHANES

[75] Inventors: Aldo Bosetti, Vercelli; Emanuele Cauchi; Vittorio Carletti, both of Novara; Pietro Cesti, Trecate, all of Italy

[73] Assignee: Ministero dell'Universita e della Ricerca Scientifica e Tecnologica, Rome, Italy

[21] Appl. No.: 09/064,166

[22] Filed: Apr. 22, 1998

[30] Foreign Application Priority Data

May 29, 1997 [IT] Italy .................................. MI97A1261

[51] Int. Cl.[7] .................................................. C07C 271/28
[52] U.S. Cl. ................................................ 560/25; 560/24
[58] Field of Search .................................. 560/24, 25, 26, 560/27, 28, 29, 32

[56] References Cited

U.S. PATENT DOCUMENTS 4,268,683  5/1981  Gurgiolo ................................... 560/24

*Primary Examiner*—Gary Geist
*Assistant Examiner*—Brian J. Davis
*Attorney, Agent, or Firm*—Oblon, Spivak, McClelland, Maier & Neustadt, P.C.

[57] ABSTRACT

A process for synthesizing aromatic urethanes, which entails:

a) reacting an organic carbonate, in an amount which is equal to or greater than a stoichiometric amount, with an aromatic amine at a temperature of 100 to 190° C.; and b) recovering the aromatic urethane from the reaction mixture, wherein step a) is carried out by maintaining reaction alcohol in an amount of from 10 to 40 mol % based on a total quantity of alcohol coproduced during the reaction.

17 Claims, 1 Drawing Sheet

PROCESS FOR THE SYNTHESIS OF AROMATIC URETHANES

BACKGROUND OF THE INVENTION

1. Field of the Invention

The present invention relates to a process for the synthesis of aromatic urethanes starting from an organic carbonate and an aromatic amine having formula (I–III), which allows high yields and selectivities to the useful reaction product.

2. Description of the Background

Aromatic urethanes (or carbamates) are valuable intermediates which can be used for the production of phytodrugs, dyes, pharmaceutical compounds and aromatic isocyanates used in the synthesis of polyurethanes.

Among aromatic urethanes, those of greatest interest, from a commercial point of view, are 4,4'-methylenediphenyldiurethane (MDA) and 2,4-toluenediurethane (TDA) used for the preparation of methylenediphenyl diisocyanate (MDI) and toluene diisocyanate (TDI), which are at present industrially produced by phosgenation of the corresponding diamines.

Processes are known for the production of urethanes which are based on the functionalization of amines with a carbonate, preferably dimethylcarbonate (DMC), in the presence of suitable catalysts according to the following scheme:

For example, U.S. Pat. No. 3,763,217 discloses the preparation, under reflux conditions, of carbamates by the reaction of an alkyl carbonate with an amine, in the presence of an acid catalyst, preferably uranyl nitrate. Under these conditions however, the conversion and selectivity yields of the carbamate are about 20%.

According to U.S. Pat. No. 4,268,683, mono- and dicarbamates are prepared by the reaction of an alkyl carbonate and an aromatic mono- or diamine, using a compound of Sn (II) or Zn (II) as Lewis acid, such as for example halides or salts of monovalent organic acids with pKa equal to or higher than 2.8, preferably zinc acetate. Operating according to this process conversion and selectivity yields of about 77% are obtained for mono-carbamate and 18–36% for dicarbamate.

U.S. Pat. No. 5,091,556 discloses a synthesis method which comprises (i) a first step in which the carbonate is reacted with an aromatic, aliphatic or cycloaliphatic monoamine, in the presence of zinc acetate, removing the alcohol produced during the reaction, to produce a mixture containing carbamate and urea, and (ii) a second step in which the mixture coming from the first step is reintegrated with the carbonate and reacted for a further 3–6 hours at 160° C. to transform the urea into carbamate.

This system allows the production of aromatic mono-carbamates with good yields and selectivities. When a diamine or aromatic polyamine is used as substrate however, the selectivity into the corresponding urethane is reduced as large quantities of ureas or polyureas are formed which cannot be quantitatively and selectively retransformed into the corresponding urethane.

In accordance with the teachings of the known art discussed above, the reaction between carbonates and amines to produce the corresponding carbamates is typically carried out by the complete removal of the reaction alcohol (U.S. Pat. No. 3,763,217 and U.S. Pat. No. 5,091,556). In fact, the accumulation of alcohol in the reaction environment causes a lowering of the synthesis kinetics and a consequent decrease in the yields to urethane owing to the secondary reactions which can become competitive under these conditions.

The object of the present invention is to obtain aromatic urethanes with high yields and selectivities, by means of a simple, economic process which can be easily effected on an industrial scale and which does not have the disadvantages of the processes of the known art.

It has now been found that this object can be reached if the reaction between the organic carbonate and the aromatic amine is carried out by the partial removal of the alcohol coproduced in the reaction.

In accordance with this, the present invention relates to a process for the synthesis of aromatic urethanes which comprises:

(a) reacting an organic carbonate, in a stoichiometric quantity or higher than the stoichiometric value, with an aromatic amine having formula (I–III):

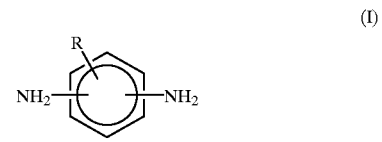

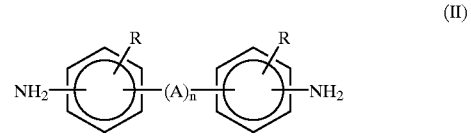

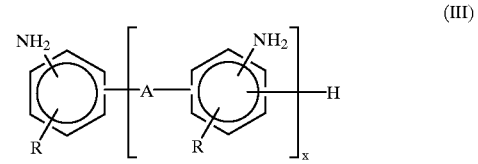

wherein: R is hydrogen, a halogen, or a hydrocarbyl or hydrocarbyloxy group with up to 8 carbon atoms, preferably up to 4, A is a divalent hydrocarbon group with from 1 to 6 carbon atoms, preferably from 1 to 4, n has a value of 0 or 1 and x has a value between 1 and 6, in the presence of a Lewis acid catalyst, at a temperature of 100 to 190° C.;

(b) recovering the urethane from the reaction mixture; wherein said process is characterized in that the reaction in step (a) is carried out maintaining the reaction alcohol within values ranging from 10 to 40% in moles with respect to the total quantity of alcohol coproduced during the reaction.

Non-limiting examples of aromatic amines having formula (I–III) are: 4,4'-methylenedianiline, 2,4'-methylenedianiline, 2,4-diaminotoluene (TDA), 2,6-diaminotoluene or mixtures of the two isomers, 1,3-diaminobenzene, 2,6-diaminonaphthalene or a polymeric methylenedianiline (mixture of isomers having formula III with x=1, 2, 3 and 4).

Organic carbonates which can be used in the process of the present invention comprise alkyl, aryl or alkyl aryl esters of carbonic acid. The ester group can be an alkyl group with up to 12 carbon atoms, preferably up to 6, or an aryl group with up to 10 carbon atoms.

Examples of organic carbonates particularly suitable for the process of the present invention are cyclic or acyclic carbonates such as for example ethylene carbonate, propylene carbonate, styrene carbonate, dimethyl carbonate, diethyl carbonate, dipropyl carbonate, dibutyl carbonate, diisopropyl carbonate, dihexyl carbonate, methyl butylcarbonate, diphenylcarbonate and methylphenylcarbonate. The organic carbonates can be prepared using the known methods.

In the process of the present invention a quantity of carbonate in excess with respect to the amine is preferably used as it also acts as solvent.

Catalysts suitable for the purposes of the present invention generally consist of Lewis acids such as bivalent tin and zinc chlorides, or salts of these metals with mono- or bi-carboxylic organic acids. Among bivalent compounds of zinc, anhydrous or dihydrate zinc acetate is preferably used.

The quantity of catalyst can vary from 20 to 0.5% in moles and preferably from 10 to 1.0% in moles per mole of amine (I–III).

The reaction temperature can vary from 100° to 190° C. Temperatures of about 140–180° C. are preferably used.

The process of the present invention, after initial pressurization with nitrogen at 1–3 absolute atmospheres (ata), is carried out at an operating pressure which is the autogenous pressure of the system and which depends on the substrate and operating conditions.

The reaction time depends on the temperature and pressure. However, reaction times of between 1 and 3 hours are sufficient.

The process of the present invention can be carried out in batch, in continuous or semicontinuous. At the end of the reaction, the product is recovered with the usual separation techniques. For example, the carbamate can be isolated by crystallization or evaporation of the solvent after elimination of the catalytic system.

The carbamoylation reaction can be carried out in a stainless steel autoclave, equipped with a distillation column arranged in series with a condenser.

In practice, the carbonate and amine can be premixed and the catalyst added to the mixture thus obtained. The whole mixture is charged into the reactor which, after initial pressurization, is brought to the operating temperature.

During the reaction a partial distillation of the alcohol is effected, in the form of an azeotropic mixture with the carbonate, so that the quantity of alcohol coproduced remaining in the reaction mixture is maintained at 10 to 40% in moles with respect to the total quantity of alcohol produced, preferably between 20 and 35% in moles.

Operating in this way, high yields and selectivities of the useful reaction product can be obtained, in a single step, in short times and with a production of urea of less than 1% by weight.

In addition, the carbonate which is removed from the reaction environment is not restored and consequently there is a concentration of the solution at the end equal to about 10%. This concentration has no negative effect on the process yield.

Finally the urethane contained in the reaction mixture is isolated and purified. The removal and consequent re-use of the carbonate is carried out by evaporation of the reaction mixture.

BRIEF DESCRIPTION OF THE DRAWINGS

In the following experimental examples which provide a better illustration of the invention, the apparatus schematically illustrated in FIG. 1 was used. In this figure (A) indicates an autoclave equipped with a stirrer and an heat-exchange devices, (B) a smooth steel condenser maintained at a temperature ranging from 80 to 150° C., preferably from 100 to 130° C. depending on the operating conditions, (C) a water condenser maintained at about 4–10° C. and (D) a collection container.

Examples 1–3 were carried out according to the present invention, whereas examples 4 and 5 are comparative.

EXAMPLE 1

Figure 1:
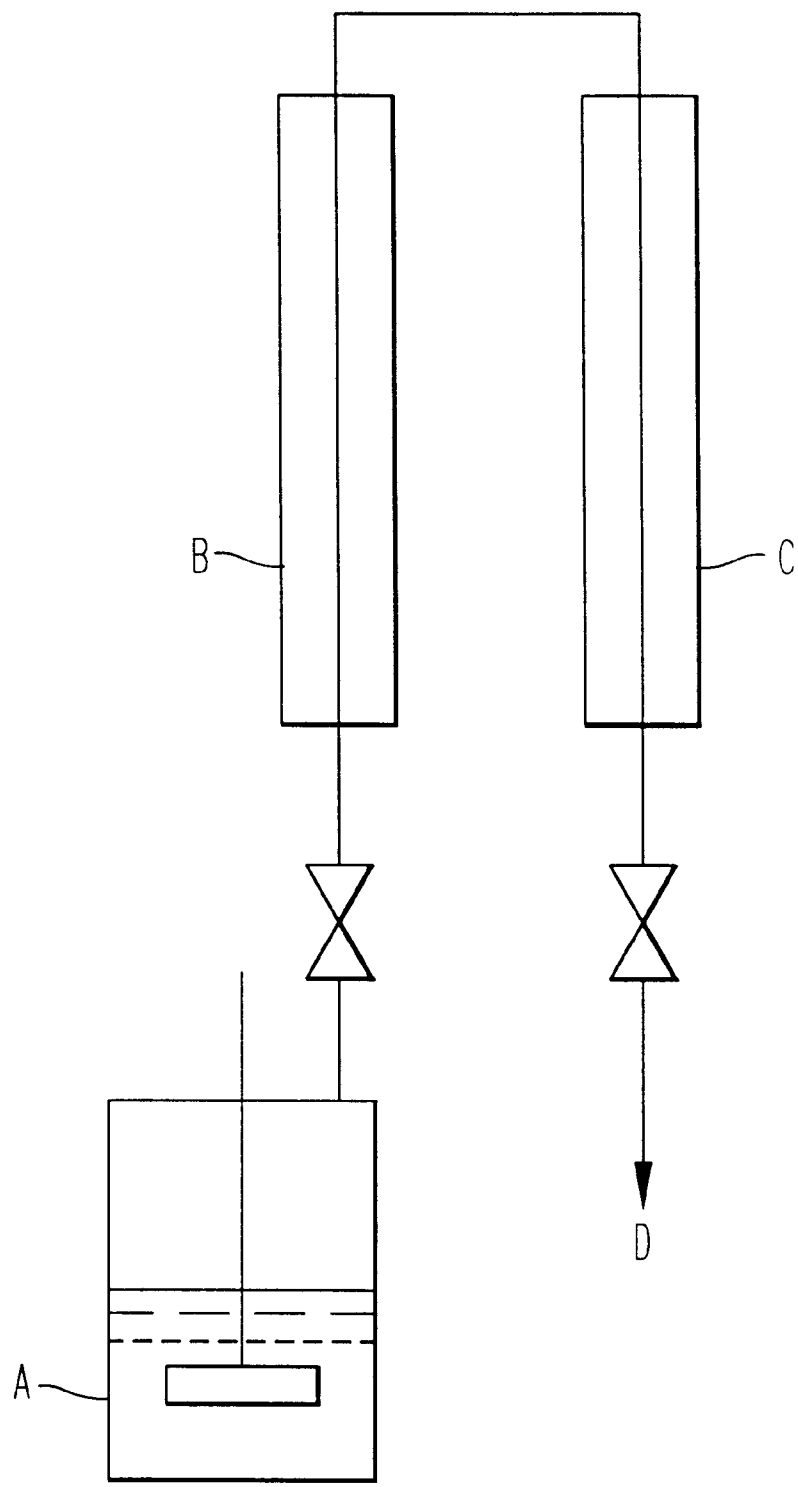

With reference to FIG. 1, 128 g (0.646 moles) of 4,4'-methylenedianiline (MDA), 1800 g of dimethylcarbonate (DMC, weight ratio DMC/MDA equal to 14) and 5 g of zinc acetate dihydrate (0.022 moles, 4% by weight with respect to the MDA, molar ratio catalyst/MDA equal to 0.034), are charged into a steel cylindrical autoclave (A) with a useful volume of 3 1.

The reactor (A) is then pressurized to 2 atm, heated so as to have an internal temperature equal to 140° C. and maintained under stirring at 300 rpm. The autoclave (A) is directly connected to the removal system of the alcohol consisting of a condenser (B) heated to about 115° C. and a condenser (C) cooled to about 10° C. The maximum pressure registered during the test is 4 ata.

After 1.5 hours, the reaction mass coming from the autoclave (A) is filtered under heat to remove the catalyst and the resulting solution is evaporated to separate the excess DMC.

The raw reaction product (203 g) thus obtained contains 197 g (97%) of 4,4'-methylenediphenyldiurethane, 4.5 g (2.2%) of N-methyl derivatives and about 1.5 g of ureas (<1% with respect to the total weight of the raw product).

From these results the following yield, conversion and selectivity values can be calculated:

conversion with respect to the initial 4,4'-MDA >99%
selectivity to 4,4'-methylenediphenyldiurethane 97%
yield 98%

At the end of the reaction the quantity of methanol present in the various parts of the equipment was also determined.

The results of the analysis gave 11 g of methanol (equal to about 27.5% in moles of the total methanol produced) in (A), 6 g in (B) and 23 g in (D). At the end of the reaction about 180 g of distillate are obtained of which 23 g of methanol (equal to about 57% of the total methanol produced), 3.4 g of methyl acetate and 153.5 g of DMC.

EXAMPLE 2

The same operating conditions are adopted as in example 1, using 140 g (1.147 moles) of toluenediamine 80/20 (TDA 80/20, mixture of 2,4- and 2,6- isomers in a proportion of 80/20), 1600 g of DMC (weight ratio DMC/TDA 80/20 equal to 11.5) and 7.6 g of zinc acetate dihydrate (0.034 moles, 5.4% by weight with respect to TDA, molar ratio catalyst/TDA 80/20 equal to 0.029).

The autoclave is then brought to 2.5 ata and an internal temperature of 170° C. The condenser (B) was set at 130° C. The maximum pressure registered during the test was equal to 9 ata. After about 2 hours at 170° C., 270 g of raw reaction product are obtained, consisting of 254 g of toluenediurethane 80/20 (mixture in a proportion of 80/20 of the respective dicarbamates of TDA 80/20), 13.8 g of a mixture of N-methylates and 2 g of insoluble ureas (equal to <1% by weight with respect to the total raw product).

From these results the following yield, conversion and selectivity values can be calculated:

conversion with respect to the initial TDA 80/20≧99%
selectivity to toluenediurethane 80/20 equal to 93%
yield 92%

At the end of the reaction, a quantity of distillate equal to 175 g was collected, of which 37 g of methanol (equal to about 55% in moles of the methanol produced), 4.5 g of methyl acetate and 133 g of dimethylcarbonate. The quantity of methanol present in the mass in the autoclave (A) at the end of the reaction was equal to 30% in moles with respect to the methanol produced.

EXAMPLE 3

The reaction was carried out under the same conditions described in example 1, using 125 g of polymeric methylenedianiline (polymeric MDA, mixture of isomers having formula III with x=1, 2, 3 and 4), 1800 g of dimethylcarbonate (DMC, weight ratio DMC/MDA equal to 14.4) and 5 g of zinc acetate dihydrate (4% by weight with respect to the polymeric MDA).

The maximum pressure registered during the test is 4 ata. After 1.5 hours of reaction at 140° C., 202.5 g of raw product are obtained consisting of 196 g of polymeric methylenediphenyldiurethane, 5 g of N-methyl derivatives and 1.5 g of insoluble ureas.

From these results the following yield, conversion and selectivity values can be calculated:
conversion with respect to the initial polymeric MDA ≧99%
selectivity to polymeric methylenediphenyldiurethane (obtained as a sum of all the isomers) 96%
yield 95%

The quantity of methanol present in the mass in the autoclave (A) at the end of the reaction was equal to 32% in moles with respect to the quantity of methanol produced.

EXAMPLE 4 (comparative)

The following products are charged into the same equipment as example 1: 128 g ((0.646 moles) of 4,4'-methylenedianiline (MDA), 1800 g of dimethylcarbonate (weight ratio DMC/MDA equal to 14) and 5 g of zinc acetate dihydrate (0.022 moles, 4% by weight with respect to the diamine, molar ratio catalyst/MDA equal to 0.034).

The apparatus is then brought to a pressure of 1. 9 ata and an internal temperature of 140° C. The condenser (B) is heated to 120° C. Under these conditions a continuous distillation is obtained of the methanol produced in the form of an azeotropic mixture with dimethyl carbonate.

The maximum pressure registered during the test is 4 ata. After about 3 hours of reaction at 140° C., the disappearance of the methanol in the reactor A is verified.

The reaction raw product, obtained as specified in example 1, was analyzed via HPLC with the internal standard method (RP-18 column, elution gradient starting from water/acetonitrile 60/40 v/v, flow 1 ml/minute) obtaining the following results:
conversion initial MDA≧99%;
selectivity to 4,4'-methylenediphenyldiurethane 88%;
ureas 8%;
by-products such as N-methylates (4%).

DMC and fresh catalyst are added to the reaction raw product so that a total of 2000 g of DMC and 5 g of zinc acetate dihydrate are present. The reaction is carried out for a further 3 hours with the procedure described above, but maintaining the internal temperature in the reactor at 160° C.

At the end of the reaction, 201.5 g of raw product are obtained, consisting of 187 g of 4,4'methylenediphenyldiurethane, 4 g of ureas and 10.5 g of N-methylate compounds. From these results the following values can be calculated:
conversion with respect to the initial MDA≧99%,
selectivity to methylenediphenyldiurethane 92%,
yield 91%.

A total of 450 g of solvent were distilled, comprising all the methanol produced during the two passages.

EXAMPLE 5 (comparative)

The reaction is carried out as described in example 1, in a closed autoclave, i.e. without removing any of the methanol produced.

The reaction is carried out for 6 hours at 140° C. The maximum pressure registered during the test proved to be equal to 6 ata. At the end of the reaction 199 g of raw product are obtained, consisting of 173 g of methylenediphenyldiurethane, 6.5 g of methylenediphenylmonourethane, 11 g of N-methylate compounds and 8.5 g of ureas.

From these results the following values can be calculated:
conversion with respect to the initial MDA≧99%,
selectivity to methylenediphenyldiurethane 85%,
yield 84%.

The results of the tests carried out using MDA are summarized in table 1 below:

TABLE 1

| Example Nr. | Time (hrs) | Removed methanol (%) | Select. to dicarb. (%) | Yield to dicarb. (%) |
|---|---|---|---|---|
| 1 | 1.5 | 72.5 | 97 | 96 |
| 4 | 6 | 100 | 92 | 91 |
| 5 | 6 | 0 | 85 | 84 |

We claim:

1. A process for synthesizing an aromatic urethane, which comprises:

a) reacting an organic carbonate, in an amount which is equal to or greater than a stoichiometric amount, with an aromatic amine having the formula (I), (II) or (III):

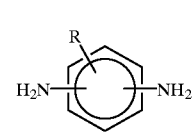

(I)

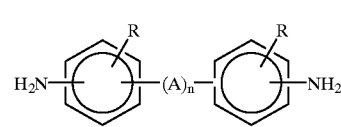

(II)

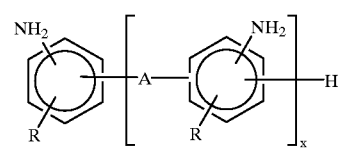

(III)

wherein R is hydrogen, halogen or a hydrocarbyl or hydrocarbyloxy group with up to 8 carbon atoms; A is a divalent hydrocarbon group with from 1 to 6 carbon atoms; n has a value of 0 or 1, and x has a value between 1 and 6, in the presence of a Lewis acid catalyst, at a temperature of 100° to 190° C.; and b) recovering the aromatic urethane from the reaction mixture;

wherein step a) is carried out by maintaining reaction alcohol in an amount of from 10 to 40 mol % based on a total quantity of alcohol coproduced during the reaction.

2. The process according to claim 1, wherein A is a divalent hydrocarbon group with from 1 to 4 carbon atoms.

3. The process according to claim 1, wherein R is a hydrocarbyl or hydrocarbyloxy group with up to 4 carbon atoms.

4. The process according to claim 1, wherein the quantity of alcohol is maintained within values ranging from 20 to 30% in moles with respect to the total quantity of alcohol produced during the reaction.

5. The process according to claim 1, wherein the carbonate is selected from ethylene carbonate, propylene carbonate, styrene carbonate, dimethyl carbonate, diethyl carbonate, dipropyl carbonate, dibutyl carbonate, diisopropyl carbonate, dihexyl carbonate, methyl butylcarbonate, diphenylcarbonate and methylphenylcarbonate.

6. The process according to claim 5, wherein the carbonate is dimethyl carbonate.

7. The process according to claim 1, wherein the aromatic amine is selected from 4,4'-methylenedianiline, 2,4'-methylenedianiline, 2,4-diaminotoluene, 2,6-diaminotoluene or mixtures of the two isomers, 1,3-diaminobenzene, 2,6-diaminonaphthalene or a polymeric methylenedianiline.

8. The process according to claim 1, wherein the acid catalyst is selected from the group consisting of bivalent tin and zinc chlorides, and salts of these metals with mono-, and bi-carboxylic organic acids.

9. The process according to claim 1, wherein the acid catalyst is anhydrous or dihydrate zinc acetate.

10. The process according to claim 1, wherein the quantity of catalyst is between 20 and 0.5% in moles per mole of amine (I–III).

11. The process according to claim 10, wherein the quantity of catalyst is between 10 and 1.0% in moles per mole of amine (I–III).

12. The process according to claim 1, wherein the reaction between carbonate and aromatic amine is carried out at a temperature ranging from 140 to 180° C.

13. The process according to claim 1, wherein said organic carbonate is reacted with said aromatic amine at a temperature of from 140 to 180° C.

14. The process according to claim 1, wherein step a) is carried out by maintaining the reaction alcohol in an amount of from 20 to 35 mol %.

15. The process according to claim 1, wherein production of urea therefrom is less than 1% by weight.

16. The process according to claim 1, wherein an excess of organic carbonate is used relative to the aromatic amine is used.

17. The process according to claim 1, wherein the reaction alcohol coproduced is methanol, and is maintained in an amount of 27.5 mol %.

* * * * *